(12) United States Patent
Bosel

(10) Patent No.: US 8,814,853 B2
(45) Date of Patent: Aug. 26, 2014

(54) THERMOCHEMICAL ABLATION NEEDLE

(75) Inventor: Christopher D. Bosel, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 972 days.

(21) Appl. No.: 12/914,188

(22) Filed: Oct. 28, 2010

(65) Prior Publication Data

US 2011/0106071 A1 May 5, 2011

Related U.S. Application Data

(60) Provisional application No. 61/255,891, filed on Oct. 29, 2009.

(51) Int. Cl.
*A61B 18/06* (2006.01)

(52) U.S. Cl.
USPC ............................... 606/28; 604/82; 604/113

(58) Field of Classification Search
CPC ............. A61B 18/06; A61B 2018/068; A61B 2018/00577; A61M 2025/0037
USPC ................. 606/27, 28; 604/82, 113, 257, 506
See application file for complete search history.

(56) References Cited

U.S. PATENT DOCUMENTS

| | | | |
|---|---|---|---|
| 4,796,622 A * | 1/1989 | Lu et al. ........................ | 606/28 |
| 4,799,479 A * | 1/1989 | Spears ........................... | 606/28 |
| 4,899,741 A | 2/1990 | Bentley et al. | |
| 4,998,933 A | 3/1991 | Eggers et al. | |
| 5,366,443 A | 11/1994 | Eggers et al. | |
| 5,385,148 A | 1/1995 | Lesh et al. | |
| 5,419,767 A | 5/1995 | Eggers | |
| RE35,330 E | 9/1996 | Malone et al. | |
| 5,620,440 A | 4/1997 | Heckele et al. | |
| 6,224,591 B1 | 5/2001 | Claren et al. | |
| 6,824,555 B1 * | 11/2004 | Towler et al. ................... | 607/96 |
| 6,832,995 B1 * | 12/2004 | Towler et al. ................... | 606/27 |
| 6,960,225 B1 | 11/2005 | Zenz et al. | |
| 7,097,642 B1 | 8/2006 | Sprague et al. | |
| 7,311,703 B2 * | 12/2007 | Turovskiy et al. .............. | 606/33 |
| 7,354,438 B2 | 4/2008 | Morgan et al. | |
| 7,422,585 B1 | 9/2008 | Eggers et al. | |
| 7,505,812 B1 | 3/2009 | Eggers et al. | |
| 7,549,989 B2 | 6/2009 | Morgan et al. | |
| 7,713,269 B2 | 5/2010 | Auge, II et al. | |
| 7,771,422 B2 | 8/2010 | Auge, II et al. | |
| 8,652,127 B2 * | 2/2014 | Prakash et al. .................. | 606/34 |
| 2005/0149010 A1 * | 7/2005 | Turovskiy et al. .............. | 606/33 |
| 2008/0243112 A1 * | 10/2008 | De Neve ......................... | 606/28 |

(Continued)

FOREIGN PATENT DOCUMENTS

WO    WO 2008/106357    9/2008

*Primary Examiner* — Linda Dvorak
*Assistant Examiner* — Jocelyn D Ram
(74) *Attorney, Agent, or Firm* — Woodard, Emhardt, Moriarty, McNett & Henry LLP

(57) ABSTRACT

There are disclosed embodiments of a system for thermochemical tissue ablation. An ablation needle in the form of a cannula with a tip and a plurality of tubes or lumens therethrough is provided, with the tip forming a hollow mixing chamber without external openings. Liquid reagents are passed through the lumens or tubes to the mixing chamber, where an exothermic reaction results, heating the tip. The heated tip is used for tissue ablation. The reaction product can be at least partially evacuated from the mixing chamber through a tube or lumen that empties into a container.

20 Claims, 4 Drawing Sheets

(56) References Cited

U.S. PATENT DOCUMENTS

| | | | |
|---|---|---|---|
| 2010/0145304 A1* | 6/2010 | Cressman | 604/506 |
| 2011/0106054 A1* | 5/2011 | Osborne et al. | 604/518 |
| 2011/0152852 A1* | 6/2011 | Cressman | 606/27 |
| 2012/0046656 A1* | 2/2012 | Brannan | 606/28 |
| 2012/0215212 A1* | 8/2012 | Selzer et al. | 606/27 |
| 2012/0323213 A1* | 12/2012 | Bates et al. | 604/500 |
| 2013/0053839 A1* | 2/2013 | Hotto et al. | 606/30 |

* cited by examiner

THERMOCHEMICAL ABLATION NEEDLE

REFERENCE TO RELATED APPLICATIONS

The present application claims the benefit of U.S. Provisional Patent Application Ser. No. 61/255,891 filed Oct. 29, 2009 entitled THERMOCHEMICAL ABLATION NEEDLE which is hereby incorporated by reference in its entirety.

The present disclosure concerns tools for ablation of tissue in medical cases by application of heat. In particular, it concerns devices in which liquid reagents are combined and maintained within the device to produce heat, which heat is applied to tissue as desired by a physician.

BACKGROUND

It is known to attack undesirable cells or growths in tissue directly to kill the growth or stop its spread. Apparatus and systems have been developed to ablate such growths through application of heat or cold, injection of chemicals, or other treatments. For example, applying sufficient heat to part or all of a cancerous or pre-cancerous growth, or injecting it with a localized toxin, kills the cells and so slows or stops the growth or spread of the problem cells. The dead cells can be collected, or the body's own mechanisms for clearing dead tissue can be allowed to eliminate those cells. Such a treatment is generally less traumatizing, painful and difficult than cutting out and removing live tissue from the body.

Injection of a toxin carries substantial risk of harming adjacent or remote tissues by absorption of the toxin. Devices for precise local application of heat or cold are generally very expensive and technically complex. In the case of heat ablation, the expense and complexity generally result from the sources of the applied heat. Radio-frequency (RF) energy, microwave energy and laser energy are common sources, and the devices to generate such energy are quite expensive. Additionally, such energy must be carefully focused on a heat-receiving medium, which may be either the tissue itself or a fluid reservoir or other medium that is heated by the energy and placed in contact with the tissue. The energy must be carefully shielded so as not to affect other tissues in the patient, or persons or equipment in proximity to the patient.

Other systems using chemical reactions in tissue treatment have been proposed. In International Publication No. WO2008/106357 A1, there is shown a device that moves an acid and a base to and out of a needle and into or adjacent to tissue. The needle has openings at the end so that the chemicals exit, emitting heat as they remain along or soak into tissue. The inventor views a drawback to this system in the emission of the chemicals into the tissue. A substantial risk of absorption of relatively concentrated acid or base into the target tissue and transmission to other tissues or the blood stream exists. The ability of tissues to take up such liquids suggests that that risk is quite high. There is also the risk that the emission of such chemicals from a needle in tissue will flow away from the target, missing it partially or completely.

U.S. Pat. No. 4,796,622 (Lu et al.) and U.S. Pat. No. 6,824,555 (Towler et al.) disclosed devices that use hydrogen and oxygen gases in the presence of a metal catalyst to generate heat. These devices are also expensive, at least because of the metals (e.g. palladium) required as catalysts in order for them to operate. Initial heating of part of the device by electricity also adds to the complexity and cost of these systems. The requirements for safe handling and supply connection of potentially explosive oxygen and hydrogen gases are substantial. The extra electrolysis structure suggested in U.S. Pat. No. 6,824,555 to provide the hydrogen and oxygen gases also adds to complexity and expense of a system. Gases' natural occupation of the entire volume they are allotted, with the pressure variations gases can undergo, means that constant gas flow and consistent pressure are needed in these systems in order to both maintain the reaction and to prevent it from propagating back toward the source of the gases. Openings from the devices are also needed as part of the gas flow path to vent unused gas and/or by-products and thereby maintaining the necessary constant gas pressure.

Accordingly, there is a need for a less expensive and less complex system for ablating tissues, while maintaining safety for the patient and others. The present disclosure meets this need.

SUMMARY

In one embodiment, a thermochemical system for ablating tissue is disclosed, which includes an elongated member having a body portion and a tip portion. The member has a plurality of discrete lumens each extending at least partially through the body portion and having respective openings facing the tip portion. The lumens can be arranged to have no direct communication between them. The tip portion defines a chamber wherein the only entrance or exit from the chamber is through the openings of the lumens. A first reservoir of a first liquid reagent is attached to one of the lumens in fluid communication, and a second reservoir of a second liquid reagent attached to one of the lumens in fluid communication. The reagents are selected so that mixing them results in an exothermic reaction without the presence of a catalyst. A container separate from the reservoirs is fluidly connected to one of the lumens. The reagents are movable from their reservoirs to mix in the chamber, reacting to form a liquid product and thereby heat the tip portion. The liquid product is removable to the container via its lumen.

The lumens to which the reservoirs are connected may be the same or separate. For example, in certain embodiments the lumen to which the first reservoir is connected is a first lumen, the lumen to which the second reservoir is connected is a second lumen separate from the first lumen, and the lumen to which the container is connected is a third lumen separate from the first and second lumens. The third lumen may lie alongside the first and second lumens, or may include a space around at least one of the first and second lumens. The lumen attached to the first reservoir, in one example, is a lumen through a first rigid tube, with the lumen attached to the second reservoir being a lumen through a second rigid tube separate from the first rigid tube, each of the tubes being fixed within the elongated member when the system is in use.

In other embodiments, the first lumen may be within the second lumen, and the second lumen may be within the third lumen. For example, the first and second lumens can come together in a single joined lumen, with the single joined lumen extending through the third lumen. In some embodiments, the third lumen outlets closer to the tip than do the first and second lumens. In particular embodiments, the first reagent is an acid (e.g. an acidic medium) and the second reagent is a base (e.g. a basic medium), or the reagents are chosen so that their mixture is exothermic absent any catalyst. The tip can have a sharpened portion directed away from the elongated member, and that sharpened portion can be configured as a distal point.

The device may further include a source of suction connected to the lumen to which the container is connected. That source of suction selectively provides suction for evacuation of the chamber. The container can include the source of suction, and in certain embodiments the container is a syringe. One or more of the reservoirs may be syringes as well.

Methods concerning the disclosed structure are also noted. Among these, a method of ablating tissue is disclosed, including providing a cannula having a tip with one or more walls defining an interior mixing chamber, the one or more walls having no openings therethrough so that matter inside the mixing chamber cannot exit through the walls. A plurality of liquid reagents is mixed in the mixing chamber, the liquid reagents being chosen so that an exothermic reaction occurs on their mixing in the absence of a solid catalyst, to warm the tip to a temperature effective for tissue ablation. The tip is placed into or against tissue to be ablated.

The cannula may include first and second separated lumens extending through it and communicating with the mixing chamber. The mixing includes passing a first liquid reagent through the first lumen and into the mixing chamber, and passing a second liquid reagent through the second lumen and into the mixing chamber. The exothermic reaction may result in at least one reaction product being in the mixing chamber, and methods can include at least partially removing the reaction product from the mixing chamber, with the removing being performed via the cannula. In certain embodiments, following the mixing, a period of time elapses during which the exothermic reaction occurs, and methods can include adding amounts of the reagents to the mixing chamber following that elapsed period of time.

These and other structures and methods are disclosed in the following text and associated drawings.

DESCRIPTION OF THE ILLUSTRATED EMBODIMENTS

Figure 1:
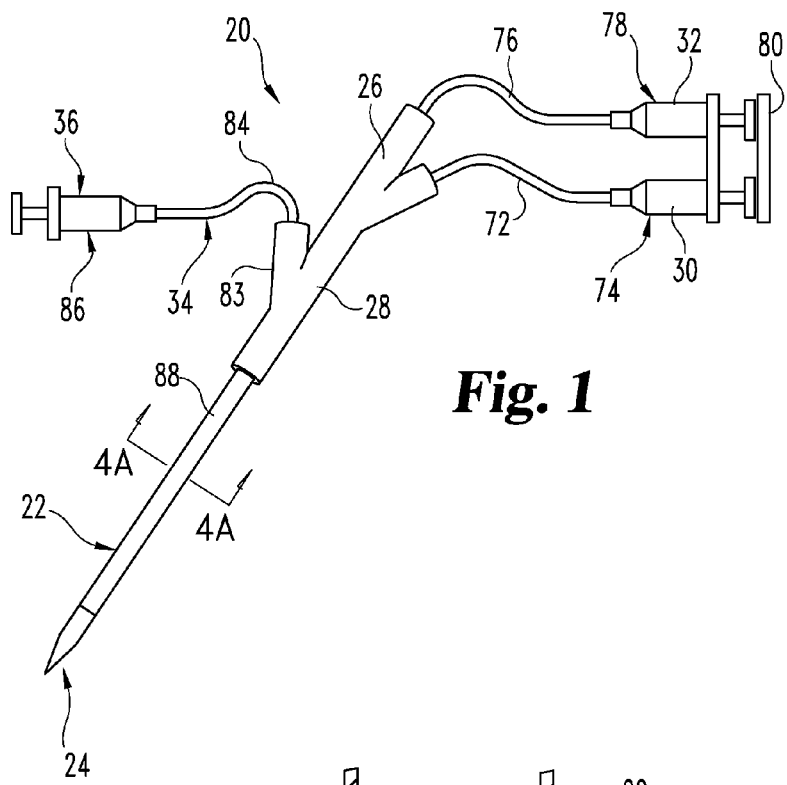
FIG. 1 is a side view of an embodiment of a system according to the present disclosure.

For purposes of promoting an understanding of the principles of the disclosure, reference will now be made to the embodiment illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein, being contemplated as would normally occur to one skilled in the art to which the disclosure relates.

Referring now generally to the Figures, there is shown an embodiment of an ablation needle system 20. System 20 includes a cannula 22 having a tip 24, with the cannula extending through or into needle hubs 26, 28. A supply of a first liquid reagent (e.g. an acid or an acidic liquid medium) 30 and a supply of a second liquid reagent (e.g. a base or a basic liquid medium) 32 are connected via needle hub 26, the supplies being non-constantly or intermittently feedable into cannula 22. An outlet 34 is connected to cannula 22 via needle hub 28. Outlet 34 may include a suction source 36.

Figure 4A:
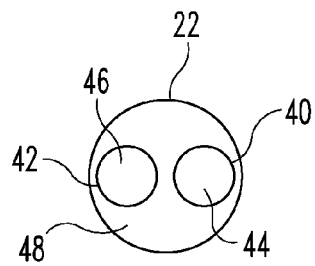
FIGS. 4A-4C are arrangements showing interiors of a portion of the system shown in FIG. 1.
Figure 4B:
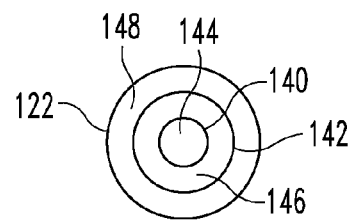
Figure 4C:
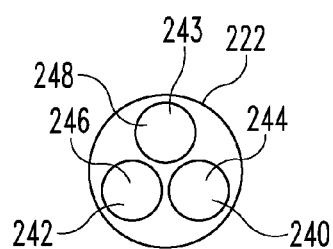
Figure 5:
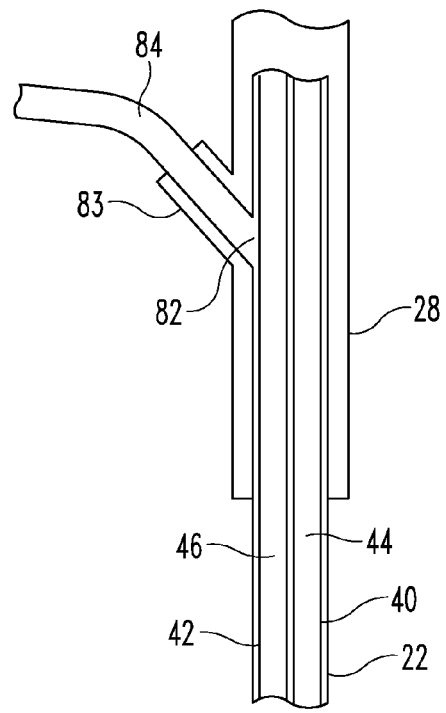
FIG. 5 is a part cross-sectional view of a part of the embodiment shown in FIG. 1.

Cannula 22 in one embodiment is a tube within which two or more additional tubes 40, 42 extend. Tubes 40, 42 communicate with supplies 30, 32, as discussed further below. Three particular configurations of cannula 22 are shown in FIGS. 4A, 4B, and 4C respectively. FIG. 4A is a cross-sectional view of a portion of FIG. 1, and shows cannula 22 as an outer tube with tubes 40 and 42 side by side within cannula 22. A first lumen 44 extends through tube 40, and a second lumen 46 extends through tube 42. A third lumen 48 is formed by cannula 22, and so it may be said that tubes 40 and 42 are within lumen 48. None of lumens 44, 46 or 48 are in direct fluid communication with either of the other lumens along their lengths, so that the contents of one lumen cannot move from that lumen directly into another.

FIG. 4B is a further alternative configuration of cannula 122, in which cannula 122 has two tubes 140 and 142, but instead of being side by side, tube 140 is within tube 142. A first lumen 144 extends through tube 140, and a second lumen 146 extends through tube 142 in the annular space between the outer surface of tube 140 and the inner surface of tube 142. A third lumen 148 extends through cannula 122 in the annular space between the outer surface of tube 142 and the inner surface of cannula 122. Each of lumens 144, 146 and 148 are separate from each other throughout cannula 122, having no passage between any two of them within cannula 122.

FIG. 4C is a further alternative configuration of cannula 222. In this embodiment, cannula 222 is an open tube that has three side by side tubes 240, 242 and 243 extending through it. Tube 240 has a lumen 244, tube 242 has a lumen 246, and tube 243 has a lumen 248. None of lumens 244, 246 or 248 are in fluid communication with either of the other lumens, as with lumens 44, 46 and 48 of FIG. 4A. In FIG. 4C, it will be seen that tubes 240, 242 and 243 (and their respective lumens 244, 246 and 248) each terminate at or about the same longitudinal point. It will be understood that tube 243 and its lumen 248, for evacuation as discussed below, may extend further or outlet closer to tip 24 than one or both of tubes 240 and 242 in other embodiments.

Further discussion of cannula 22 will refer to the embodiment of FIG. 4A for the sake of clarity and conciseness. It will be seen, however, that this discussion is equally applicable to other embodiments, including those of FIGS. 4B and 4C. Tubes 40 and 42 are fixed within cannula 22 in this embodiment, at least during use of system 20, and each of tubes 40 and 42 may be made of a surgical grade metal (e.g. stainless steel) or similar rigid and sturdy material.

Tip 24 is monolithic with cannula 22 in the illustrated embodiment, so that cannula 22 is a one-piece closed-end elongated tube or needle. Tip 24 is hollow with a wall 52 having a substantially uniform thickness in this embodiment, as well as inner surface 54 and outer surface 56. In a particular embodiment, tip 24 has a conical section 58 that narrows to a point 60. Tip 24 is of a material suited to efficient transfer and distribution of heat, and in one embodiment may be of a surgical grade metal such as stainless steel. The material of tip 24 and cannula 22 is uniform in certain embodiments so as to uniformly distribute heat, limiting the presence of hot or cold spots in tip 24 as much as possible. Point 60 is sharp in this embodiment so as to enable more accurate and direct application of heat for ablation and to allow easier penetration into tissue.

Figure 8:
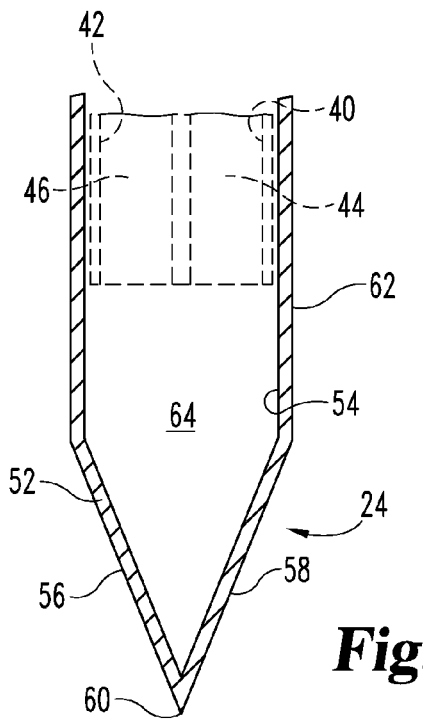
FIG. 8 is a close-up part cross-sectional view of a distal end of the system similar to that shown in FIG. 7.

In other embodiments (see, e.g., FIG. 8), tip 24 is configured substantially as discussed above, but is initially separate from cannula 22, and is placed over a distal end of cannula 22 in a sealed engagement. Such a tip 24 includes a proximal portion 62 that is substantially cylindrical, having an inner diameter at least large enough to create an interference fit with the distal end of cannula 22, creating a fluid-tight seal between tip 24 and cannula 22. If such a direct interference fit is not provided, a seal may be created by threads, such as a female thread (not shown) inside proximal portion 62 of tip 24 and a male thread (not shown) on the outside of cannula 22. Other alternatives for sealing include an adhesive, weld or other join between tip 24 and cannula 22, or a separate O-ring (not shown) or other sealing piece may be inserted between or around them. The engagement of tip 24 to cannula 22 provides a liquid-tight seal between the inner surface 54 of tip 24 and the distal end of cannula 22.

Tip 24 forms a liquid-tight chamber 64 within its inside surface 54. Chamber 64 provides a mixing area for reagents, as discussed further below, and so the use of stainless steel for tip 24 has the advantage of limited reaction with many reagents, and thus limited interference with a reaction occurring within chamber 64. When the reagents 30, 32 join and mix in chamber 64, an exothermic reaction results, without the necessity of any solid catalyst or mediator present in chamber 64. The reaction heats tip 24 substantially uniformly, and heated tip 24 can then be used to ablate tissue.

As noted above, cannula 22 (in one example in FIG. 4A) includes tubes 40 and 42, which in the illustrated embodiment are fixed or sealed to the inside of cannula 22 at least when system 20 is in use. In certain embodiments, tubes 40 and 42 may be easily inserted or removed from cannula 22. Tubes 40 and 42 run side by side through cannula 22 and are substantially parallel to each other and to cannula 22 in the illustrated embodiment, and each of tubes 40, 42 has a respective distal end that is substantially flush with the distal end of cannula 22. Thus tubes 40, 42 do not enter chamber 64 in that embodiment. Tubes 40, 42 extend up through hub 28 and into hub 26, and are connected to the respective supplies of reagents 30, 32. In one example, a flexible conduit 72 connects syringe 74 to tube 40. Syringe 74 is one example of a container for the supply of reagent 30, and it will be understood that a variety of other containers might be used in addition to or in place of a syringe. Likewise, a flexible conduit 76 connects syringe 78 to tube 42, with syringe 78 being one example of a container for reagent supply 32. The respective plungers of syringes 74, 78 may be connected together by a rigid connector 80 so that pressure on connector 80 will compress both plungers.

Conduits 72, 76 are sealed with respect to their respective tubes 40, 42 so as to limit or prevent loss of reagents. Conduits 72, 76 may be permanently sealed into their respective tubes 40, 42, or they may be insertable in tubes 40, 42 in connection with a washer or other seal or a luer lock connection so as to be easily removable from the respective tubes. Tubes 40, 42 are rigid in the illustrated embodiments, as previously noted, while in other embodiments they may be made of flexible materials such as plastic, rubber or similar materials. Tubes 40, 42 provide separate lumens for passage of reagents 30, 32 to chamber 64.

Cannula 22 forms a passage 48 away from chamber 64 in the space outside of tubes 40, 42. An opening 82 in cannula 22 coincides in the illustrated embodiment with a branch in hub 28. A conduit 84 communicates with opening 82 and/or cannula 22. In the embodiment shown in FIG. 1, a syringe 86 is connected to conduit 84 to provide intermittent or non-continuous suction, as discussed further below. In other embodiments, conduit 84 may join to or empty into a vial, bag or other closed or open container C (see FIG. 2). Conduit 84 is sealed fluid-tightly to opening 82 to limit or prevent seepage or leakage of fluid.

In the illustrated embodiment, cannula 22 is at least partially enclosed in a layer of insulation 88. Insulation 88 extends from the lower end of hub 28 to a point above the conical tapering of tip 24. A portion of cannula 22 at or above hub 28 is held by the hand of the physician or other operator, in one embodiment, with insulation 88 covering a portion of cannula 22 that is within or adjacent tissue not targeted for ablation. Accordingly, such tissue is protected from the heat generated in and applied by tip 24. In cases in which cannula 22 is inserted directly through skin or other tissue (e.g. not via an incision or other opening), it is likely that a portion of cannula 22 above tip 24 will contact skin or other tissue, and insulation 88 prevents damage to that contacted tissue. It will be understood that insulation 88 may be extended up cannula 22 to provide an insulated area for gripping by the operator's hand. Tip 24 is left uncovered for direct application of heat to the specific area in which ablation is desired.

Reagents 30, 32 are a relatively strong acid and a relatively strong base in certain embodiments. A particular embodiment uses sodium hydroxide (NaOH) and hydrochloric acid (HCl) as reactants that will provide adequate heat for ablation, without the need for any catalyst. The reagents are in liquid form to eliminate problems associated with devices that bring gases such as hydrogen and oxygen together for heat, among which is notably the need for an expensive solid metal catalyst in the reaction area. Other liquid acids and bases (or liquid media that are respectively acidic and basic) can be used in system 20, as well as other liquid reagent combinations that produce exothermic reactions.

System 20 is prepared by loading in supplies of reagents 30, 32. For example, if syringes 74 and 78 are used, they can be filled with the necessary reagents prior to insertion of their respective plungers, or by filling through an auxiliary port (not shown), as by the types of vials used for transporting and/or dispensing standard medications. Alternatively, syringes 74 and 78 (or vials as just noted) previously filled with the necessary reagents can be provided and connected to respective conduits 72, 76, as by direct insertion or by connection through a luer lock connection such as those used for catheters or needles. If syringe 86 is used, it also is connected by insertion into conduit 84, by luer lock connection, or by inserting the already-connected combination of syringe 86 and conduit 84 into opening 22. If syringe 86 is not used, conduit 84 may be connected to or placed so as to empty into a container, as indicated above.

Frequently ablation is used to kill and/or remove cancerous or other unhealthy tissue, and so access must be gained to the particular site of such tissue. When system 20 is prepared for use, the surgeon or other medical practitioner obtains access to the site of tissue to be ablated. If the ablation site is internal, then cannula 22 may be inserted directly into tissue, akin to uses of a standard needle, particularly if end portion 60 is pointed or tip 24 is otherwise sharpened to an extent similar to a standard needle. Alternatively, minimally-invasive (e.g. laparoscopic) techniques may be used to enable insertion of cannula 22, or in other cases a more open surgical technique can be used. If, as discussed above, end portion 60 and/or other aspects of tip 24 are pointed or sharpened, they can be used to part or pierce tissue between the minimally-invasive or other opening to get to a desired ablation site.

When the desired access is obtained and cannula 22 is advanced to the site, in the illustrated embodiment connector 80 is pressed to push in both plungers of syringes 74, 78. Doing so pushes liquid reagents 30, 32 through the respective conduits 72, 76 and tubes 40, 42, so that a volume of each reagent 30, 32 enters chamber 64 and they are mixed. Reagents 30 and 32 preferably react with each other immediately, without the presence of a solid catalyst against which they are passed or the addition of heat or other types of energy, producing an exothermic reaction. Heat from the reaction is conveyed into walls 52 of tip 24, and along some or all of cannula 22, causing tip 24 to become hot enough for ablation.

It will be understood that the pressing of plungers of syringes 74, 78 can occur prior to insertion of cannula 22 into the patient, at a time when tip 24 is adjacent the tissue to be ablated, or at an intermediate point in time. An advantage of moving reagents 30, 32 into chamber 64 prior to insertion into the patient is that tip 24 then has time to come to an equilibrium temperature (such as the 40-43 degrees Celsius or more needed for effective ablation in some circumstances) as the cannula is being inserted. An advantage to waiting until cannula 22 is adjacent the ablation site for mixing reagents 30, 32 is that there is little or no heat in tip 24 as it is placed, and thus little or no danger of heat injury to tissue on the way to the ablation site. This may be a particularly important consideration when tip 24 is used as a cutting or penetration tool for moving through tissue to an ablation site.

With tip 24 heated from within by the exothermic reaction, tip 24 is placed against or within tissue to be ablated for a period sufficient to kill the tissue. The conical or pencil-point shape of tip 24 allows a relatively long sloped side to be placed against tissue, or a narrowly-directed point to be used to ablate a very small area. The point of tip 24 also allows penetration into a tumor, for example, so that substantially the whole surface area of tip 24 contacts tissue to be ablated.

After the reagents 30, 32 have been in chamber 60 for a sufficient time, the exothermic reaction they undergo will wind down to a point at which the amount of heat provided to the walls 52 of tip 24 is insufficient to maintain the temperature needed for ablation. At or before that point, the operator can at least partially remove (e.g. by applying suction) the reaction product (in the case of acid-base reactions, principally water) through the passage or lumen 48 in cannula 22 outside of tubes 40, 42. By pressing further on the plungers of syringes 74, 78, more reagents 30, 32 are forced into chamber 64, displacing the reaction product from chamber 64 into passage 48 of cannula 22. If syringe 86 is provided, then additionally or alternatively the user can apply selective suction by pulling out on the plunger of syringe 86, drawing reaction product out of chamber 64 and into passage 48, and helping to draw additional reagents 30, 32 from tubes 40, 42 into chamber 64 to continue or reinvigorate the reaction. Pressure and/or suction in these manners force reaction product up through passage 48 and opening 82 into conduit 84 and syringe 86. If syringe 86 is not provided, conduit 84 empties into a container C as indicated above. Forcing additional amounts of reagents 30, 32 into chamber 64 pushes reaction product into lumen 48 and eventually through conduit 84 and into the container. Accordingly, the system 20 is adapted to recharge the reaction and at least partially evacuate reaction product by selective activation by the user. Heat sufficient for ablation is maintained in tip 24, without the presence of a catalyst or the necessary constant suction or venting of gases.

In the illustrated embodiment, system 20 is a closed system, i.e., closed to the atmosphere. In that embodiment, pressure on connector 80 on syringes 74, 78 and suction from syringe 86 occur together. That is, pressing on connector 80 forces the plunger of syringe 86 outward because of internal pressure, and pulling out the plunger of syringe 86 forces the plungers of syringes 74, 78 inward because of external atmospheric pressure. In the illustrated embodiments or others, a vent (not shown) may be placed to assist with evacuation of chamber 64. As one example, in an embodiment using a third tube or lumen (e.g. tube 243) and having one or more of syringes 74, 78 and 86, a vent (not shown) may be placed in cannula 222 above the level of reaction product (e.g. above the junction of cannula 222 with a conduit like conduit 84). Tubes 240, 242 remain unvented in this example, so that liquid in tubes 240, 242 remains therein. In such embodiments, pulling out the plunger of syringe 86 reduces pressure in tube 243, allowing atmospheric pressure through the vent to push reaction product out of chamber 64 and into and through tube 243. It will also be understood that maintaining or adding pressure on connector 80 (i.e. on one or both plungers of syringes 74, 78) can assist to force liquid out of chamber 64 as well.

Once the ablation procedure is completed, cannula 22 can be withdrawn from the surgical site. The remaining reagents 30, 32, if any, can be easily disposed of or saved for future procedures. The evacuated reaction product can also be disposed of. System 20 can be made for one-time use, although it will be seen that all or part of system 20, including syringes, conduits and cannula, could be cleaned, sterilized and re-used.

It will be understood that the embodiments shown in FIGS. 4B and 4C operate in substantially the same way as described above. In the case of the FIG. 4B embodiment, separate tubes 140, 142 have separate connections to conduits and syringes or other supplies of reagents 30, 32. One reagent moves through the lumen of tube 140, and the other through the lumen of tube 142 outside of tube 140. Evacuation of reactant product, as discussed above, takes place via lumen or passage 148. In the case of the FIG. 4C embodiment, tubes 240 and 242 operate just as described above with respect to tubes 40 and 42. A third tube 243 within cannula 22 acts as the evacuation route, and is connected to conduit 84 as discussed above.

Figure 6:
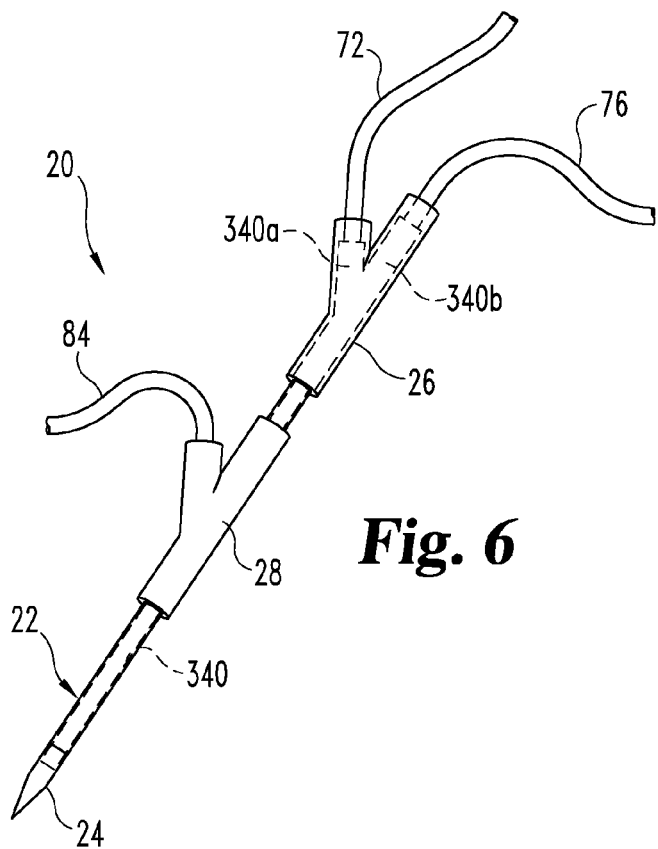
FIG. 6 is a side view of the embodiment shown in FIG. 1 with alterations.

Another embodiment of system 20 is shown in FIG. 6, which features a single tube 340 that branches at a proximal end into tube ends 340a and 340b. Conduits 72, 76 each enter respective tube ends 340a, 340b, as described above, and tube ends 340a, 340b join in or near hub 26 into a single tube 340 that extends through hub 28 and cannula 22. Reagents 30 and 32 have some contact with each other as they pass into and through tube 340 to chamber 64. Thus, there is a reaction between the reagents that occurs in tube 340, as well as in chamber 64 in this embodiment. Evacuation of reaction product can be accomplished as described above with respect to any of the embodiments.

Figure 7:
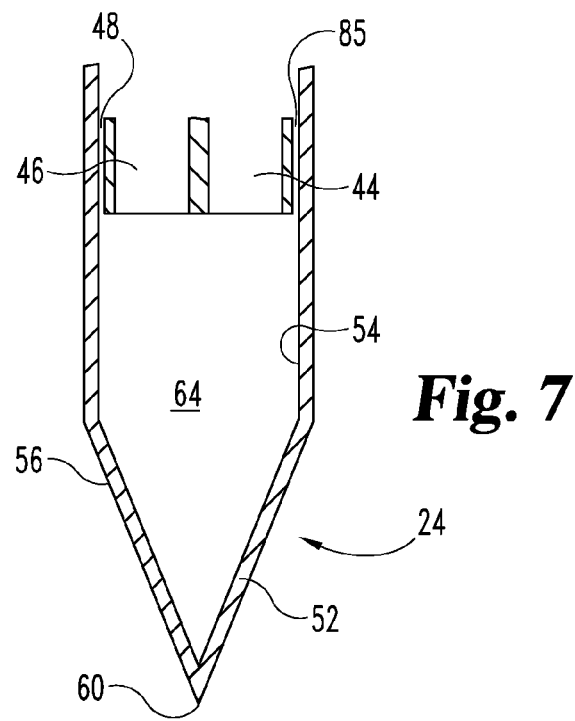
FIG. 7 is a close-up cross-sectional view of a distal end of the system similar to that shown in FIG. 3.

In the above-described embodiments, the tubes (e.g. tubes 40, 42, 140, 142, 240, 242, and/or 243) as well as cannula 22 are rigid tubes of metal. The rigidity makes system 20 easy to hold, manipulate and position in direct insertion, minimally-invasive or open surgical ablation techniques. It will be understood that one or more (or all) of the tubes and/or cannula 22 may alternatively be flexible tubes. A flexible cannula 22 can enable the device to be moved into and through a body organ or vessel. Further, cannula 22 may be formed as a rigid or flexible hose with one or more tubes (e.g. tubes 40, 42, 140, 142, 240, 242, and/or 243) formed as lumens through the hose. In other words, rather than having tubes that are pieces initially separate from cannula 22, as described above, the tubes may be discrete lumens through a catheter or similar device. Reagents may be passed through those discrete lumens, as with the lumens of tubes 40, 42 into chamber 64 for reaction, and product can be evacuated through another lumen as with the lumen of tube 243 (FIG. 4C) or passage 48 (FIG. 4A or FIG. 7) of embodiments of cannula 22. As seen in one example in FIG. 7, hose or catheter 85 is fixed within cannula 22 and has lumens 44 and 46 which are or will be respectively connected to reagent supplies 30 and 32 as discussed above. As with tubes 40, 42, reagents 30, 32 move to chamber 64 via lumens 44 and 46 that extend through hose or catheter 85. Another lumen or opening in or around hose 85 (e.g. laterally adjacent to one or both of lumens 44, 46) can be used to move reaction product out of chamber 64, as described above with respect to passage 48 and tube 243.

Figure 9:
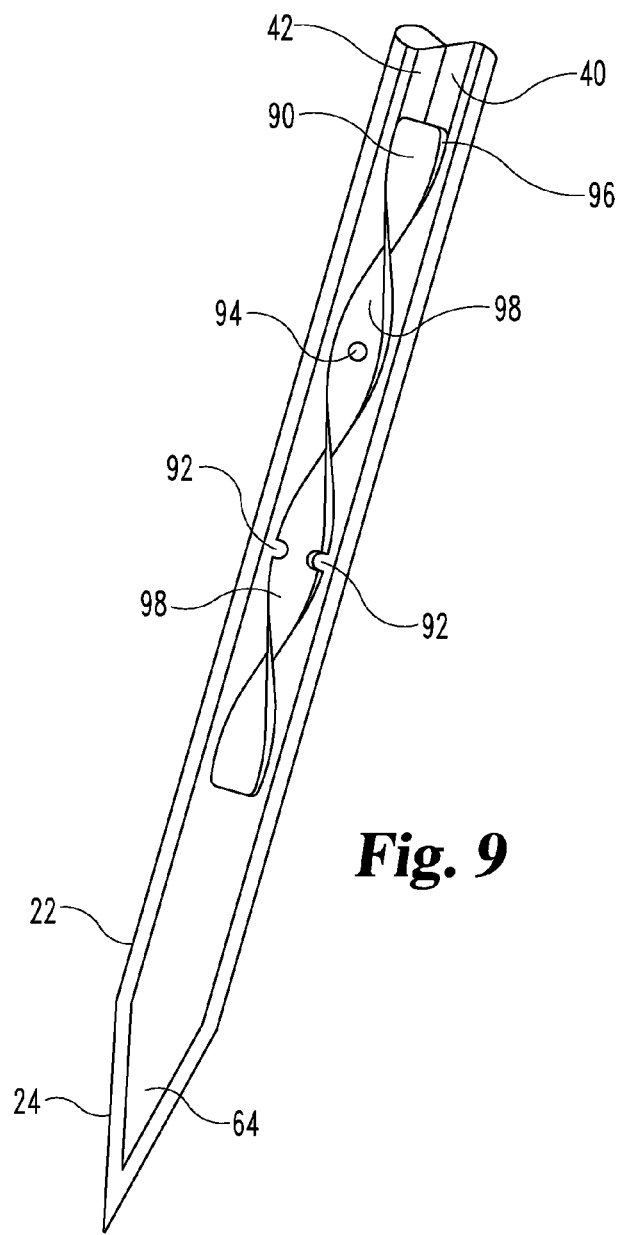
FIG. 9 is a view as in FIG. 1 showing the presence of additional structure.

Referring to FIG. 9, in certain embodiments system 20 can include an internal mixing feature 90 to assist the mixing of reagents 30, 32. For example, in the illustrated embodiment mixing feature 90 is a spiral mixer that optionally includes notches 92 and/or aperture(s) 94, and has a helically-twisted blade or web (e.g. of plastic or metal) placed above at least a portion of chamber 64. Other embodiments can use mixing feature(s) with other mixer configurations, including but not limited to a flow dividing static mixer, an alternating spiral mixer, and a static mixer with overlapping semi-helical baffles. Mixing feature 90 is attached to or integrally formed with the end(s) of one or both of tubes 40, 42 in this embodiment, but may also be attached to the side of cannula 22, and/or the inside of tip 24. In other embodiments, mixing feature 90 could also float in or above chamber 64. If it is attached or integrally formed with a portion of system 20, mixing feature 90 is accordingly rotationally constrained with respect to one or more of cannula 22, tip 24 and tubes 40, 42. Alternatively, mixing feature 90 can be rotatably connected with respect to cannula 22, tip 24 and/or tubes 40, 42, and such rotation can be driven by the flow of reagents 30 and 32 as they exit tubes 40, 42.

Figure 2:
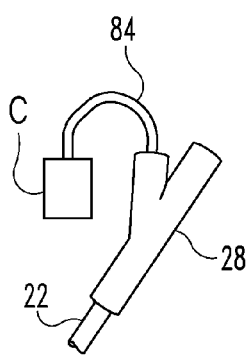
FIG. 2 is a partial side view of the system shown in FIG. 1 with an alternate container for holding reaction product.

FIG. 9 shows structure as in the embodiment of FIG. 1, and includes mixing feature 90 between the ends of tubes 40, 42 and a substantial portion of chamber 64. In that embodiment, mixing feature 90 has an end 96 and describes helical grooves or paths 98 on either side along its length. End 96 is positioned so as to intersect or be immediately below the openings of tubes 40, 42, so that a portion of the outflow from each tube will be on each side of mixing feature 90. Mixing feature 90 promotes intermixture of reagents 30 and 32 and so promotes a reaction between them. As reagents 30, 32 move together around paths 98, swirling or turbulence mixes reagents 30, 32. While reagents 30, 32 can mix in chamber 64 without mixing feature 90, it is believed that mixing feature 90 starting the mixing before reagents 30, 32 fully arrive in chamber 64 may start the exothermic reaction more quickly and use the reactants more thoroughly and efficiently. The disclosure of U.S. application Ser. No. 12/914,167 entitled MULTI-LUMEN MEDICAL MIXING DEVICE, naming Thomas Osborne, Jeff Melsheimer and Christopher Bosel as inventors and filed concurrently with this application, is incorporated by reference herein in its entirety.

Figure 3:
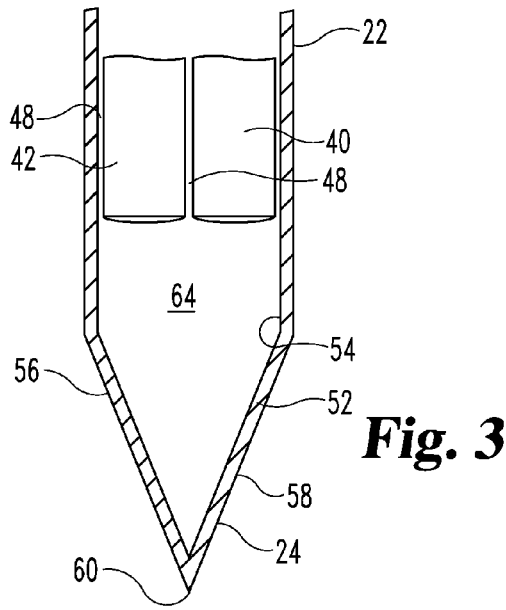
FIG. 3 is a close-up part cross-sectional view of a distal end of the system shown in FIG. 1.

It will be understood that structure as in the embodiment of FIG. 6 can also include a mixing feature as described above within tube 340 and/or between tube 340 and tip 24. Insofar as tube 340 is somewhat longer than the space between tubes 40, 42 and the walls of tip 24 as shown in FIG. 3, mixing feature 90 may be substantially longer if placed in tube 340. As noted above, the helical paths 98 provide helical motion and turbulence to the reagent flow, affirmatively mixing reagents 30, 32 as they progress along tube 340.

As noted above, continued pressure on syringes 74, 78 and/or suction via syringe 86 moves the mixed reagents 30, 32 from chamber 64 and supplies fresh reagents 30, 32 to chamber 64. In a closed system, pressure on syringes 74, 78 creates a high internal pressure (relative to atmospheric pressure) that forces the plunger of syringe 86 outward to accommodate mixed reagents, and pulling the plunger of syringe 86 generates a low internal pressure (relative to atmospheric pressure) that draws reagents 30, 32 from syringes 74, 78, at least to the extent that such internal pressure changes overcome friction or other forces in or on the syringe(s). In a vented system, evacuation to syringe 86 or other container may result from affirmative suction, e.g. via pulling the plunger of syringe 86. Whether closed or vented, suction and/or positive pressure may be continuous, so as to help provide consistent mixing and turnover of reagents 30, 32, or may be non-continuous or intermittent, with the operator more closely controlling the reaction in the system.

It will also be understood from this disclosure that the liquid reagents noted herein can include acids, bases, and respective liquid media that include an acid or a base. Such liquid media may also include a catalyst or catalytic substance in the medium (e.g. in solution) to improve or affect the reaction between or among the reagents.

While embodiments have been illustrated and described in detail in the drawings and foregoing description, the same is to be considered as illustrative and not restrictive in character, it being understood that only those embodiments have been shown and described and that all changes and modifications that come within the spirit of the disclosure are desired to be protected.

What is claimed is:

1. A liquid thermochemical system for ablating tissue, comprising:
an elongated member having a body portion and a tip portion, said member having a plurality of discrete lumens each extending at least partially through said body portion and having respective openings facing said tip portion, said tip portion defining a chamber wherein the only entrance or exit from said chamber is through the openings of said lumens;
a first reservoir of a first liquid reagent attached to one of said lumens in fluid communication;
a second reservoir of a second liquid reagent attached to one of said lumens in fluid communication, said first and second reagents being selected so that mixing said reagents results in an exothermic reaction without the presence of a solid catalyst; and
a container separate from said reservoirs fluidly connected to one of said lumens,
wherein said first and second liquid reagents are movable from said reservoirs to mix in said chamber to react to form a liquid product and thereby heat said tip portion, and wherein said liquid product in said chamber is evacuatable to said container via said lumen fluidly connected to said container.

2. The system of claim 1, wherein said lumen to which said first reservoir is connected is a first lumen, said lumen to which said second reservoir is connected is a second lumen separate from said first lumen, and said lumen to which said container is connected is a third lumen separate from said first and second lumens.

3. The system of claim 2, wherein said third lumen lies alongside said first and second lumens.

4. The system of claim 2, wherein said third lumen comprises a space around at least one of said first and second lumens.

5. The system of claim 2, wherein said first lumen is within said second lumen, and said second lumen is within said third lumen.

6. The system of claim 2, wherein said third lumen outlets closer to said tip than said first and second lumens.

7. The system of claim 2, wherein said first and second lumens join into a single joined lumen, and said single joined lumen extends through said third lumen.

8. The system of claim 1, wherein said first reagent is an acid and said second reagent is a base.

9. The system of claim 1, wherein mixture of said reagents provides an exotherm absent any catalyst.

10. The system of claim 1, wherein said tip has a sharpened portion directed away from said elongated member.

11. The system of claim 10, wherein said sharpened portion is a distal point.

12. The system of claim 1, further comprising a source of suction connected to said lumen to which said container is connected, said suction being selectively provided for evacuation of said chamber.

13. The system of claim 12, wherein said container includes said source of suction.

14. The system of claim 13, wherein said container is a syringe.

15. The system of claim 1, wherein at least one of said reservoirs are syringes.

16. The system of claim 1, wherein said lumen attached to said first reservoir is a lumen through a first rigid tube, and said lumen attached to said second reservoir is a lumen through a second rigid tube separate from said first rigid tube, said first and second tubes being fixed within said elongated member when said system is in use.

17. A method of ablating tissue, comprising:

providing a cannula having a tip with one or more walls defining an interior mixing chamber, said one or more walls having no openings therethrough so that matter inside the mixing chamber cannot exit through said one or more walls;

mixing a plurality of liquid reagents in said mixing chamber, said mixing causing an exothermic reaction in the absence of a solid catalyst, said exothermic reaction heating said tip to a temperature suitable for tissue ablation; and placing said tip into or against tissue to be ablated.

18. The method of claim 17, wherein said cannula includes first and second separated lumens extending through the cannula and communicating with said mixing chamber, and said mixing comprises passing a first of said liquid reagents through said first lumen and into said mixing chamber and passing a second of said liquid reagents through said second lumen and into said mixing chamber.

19. The method of claim 17, wherein the exothermic reaction results in at least one reaction product in said mixing chamber, and further comprising at least partially evacuating said reaction product from said mixing chamber, said evacuating being performed via said cannula.

20. The method of claim 17, wherein following said mixing, a period of time elapses during which the exothermic reaction occurs, and further comprising adding amounts of said reagents to said mixing chamber following that elapsed period of time.

* * * * *